United States Patent
Neseem

(10) Patent No.: US 8,197,429 B2
(45) Date of Patent: Jun. 12, 2012

(54) DOUBLE ARM SLING

(76) Inventor: Kahkashan Neseem, Arlington, VA (US)

(*) Notice: Subject to any disclaimer, the term of this patent is extended or adjusted under 35 U.S.C. 154(b) by 152 days.

(21) Appl. No.: 12/770,963

(22) Filed: Apr. 30, 2010

(65) Prior Publication Data
US 2011/0218468 A1   Sep. 8, 2011

Related U.S. Application Data

(60) Provisional application No. 61/310,485, filed on Mar. 4, 2010.

(51) Int. Cl.
*A61F 5/00* (2006.01)
(52) U.S. Cl. .......................................................... 602/4
(58) Field of Classification Search ................ 602/1, 4; 128/845, 846, 873–875
See application file for complete search history.

(56) References Cited

U.S. PATENT DOCUMENTS

| | | | | |
|---|---|---|---|---|
| 2,560,243 | A | * | 7/1951 | Peterson .......................... 602/4 |
| 3,559,640 | A | * | 2/1971 | Beckett ............................ 602/4 |
| 4,526,164 | A | * | 7/1985 | Bihl ................................. 602/4 |
| 4,674,664 | A | * | 6/1987 | Simon ........................... 224/604 |
| 5,558,626 | A | | 9/1996 | Holtzman et al. |
| 6,190,340 | B1 | | 2/2001 | Borell |
| 6,435,185 | B1 | | 8/2002 | Schimpl |
| 6,966,069 | B2 | | 11/2005 | Booth |
| 7,037,281 | B1 | | 5/2006 | Jeffrey et al. |

* cited by examiner

*Primary Examiner* — Michael A. Brown
(74) *Attorney, Agent, or Firm* — Maier & Maier, PLLC

(57) ABSTRACT

A double arm sling, including two pouches, each of the two pouches configured for individually receiving one of a patient's arms, and at least one pair of half-straps, the at least one pair of half-straps configured to fasten the double arm sling around the torso of the patient. The double arm sling may further include at least one pair of tongues coupled to the two pouches and coupled to the at least one pair of half-straps, a backing portion coupled to the two pouches, and at least one back pad configured to receive the at least one pair of half straps.

8 Claims, 4 Drawing Sheets

DOUBLE ARM SLING

RELATED APPLICATIONS

The present invention claims priority under 35 U.S.C. §120 to U.S. Provisional Patent Application No. 61/310,485, filed on Mar. 4, 2010, the disclosure of which is incorporated by reference herein in its entirety.

BACKGROUND

Patients suffering from amyotrophic lateral sclerosis (ALS), commonly known as Lou Gehrig's disease, generally experience severe progressive degeneration of motor neurons, resulting in the loss to the patient of voluntary muscular control. The lack of neuronal communication with the patient's muscles results in the weakening and eventual atrophy of the muscles.

Certain ALS patients may retain control of certain muscle groups, while other muscle groups may atrophy. For example, arm flaccidity is common among ALS patients. Without the ability to control their arms, ALS patients with arm flaccidity are essentially burdened with dead weight that exerts force on the musculoskeletal system of the shoulder area. Left unmitigated, arm flaccidity may result in bilateral subluxation of the shoulder joints as well as weakness of the neck. For example, the humeral head may be dislocated from the glenoid fossa of the scapula, resulting in increased pain for the patient as well as further deterioration of the arm muscles.

Arm slings and other devices for arm support are generally directed towards supporting only one of the patient's arms, and, furthermore, generally distribute the weight of the patient's arm over and through the patient's neck and shoulders. However, ALS patients having arm flaccidity not only require support of both arms but furthermore suffer from weakness and increased pain in the neck and shoulder area, making the use of conventional arm slings painful and unfeasible.

SUMMARY

According to one exemplary embodiment, a double arm sling is described. The double arm sling may including two pouches, each of the two pouches configured for individually receiving one of a patient's arms, and at least one pair of half-straps, the at least one pair of half-straps configured to fasten the double arm sling around the torso of the patient. The double arm sling may further include at least one pair of tongues coupled to the two pouches and coupled to the at least one pair of half-straps, a backing portion coupled to the two pouches, and at least one back pad configured to receive the at least one pair of half straps.

According to another exemplary embodiment, a method of using a double arm sling is described. The method may include donning a double arm sling on a patient, unsealing each of two pouches of the double arm sling, placing a first arm of the patient into a first pouch of the two pouches, sealing the first pouch of the two pouches, placing a second arm of the patient into a second pouch of the two pouches, and sealing the second pouch of the two pouches.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
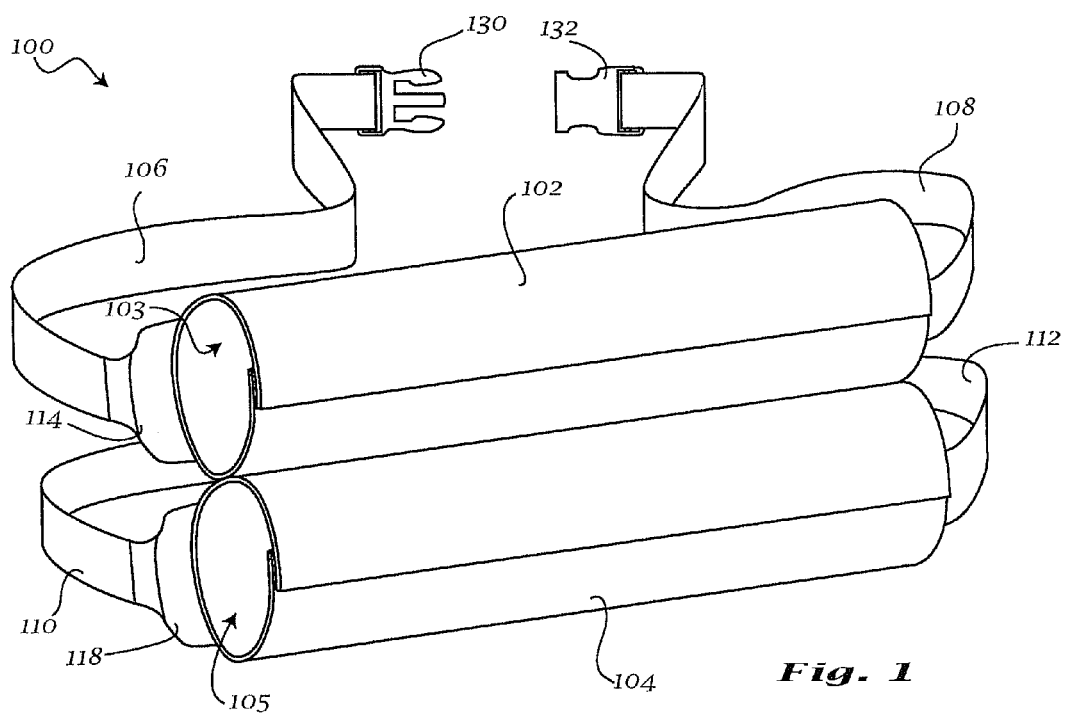
FIG. 1 is a front view of an exemplary embodiment of an arm sling in a closed configuration.
Figure 2:
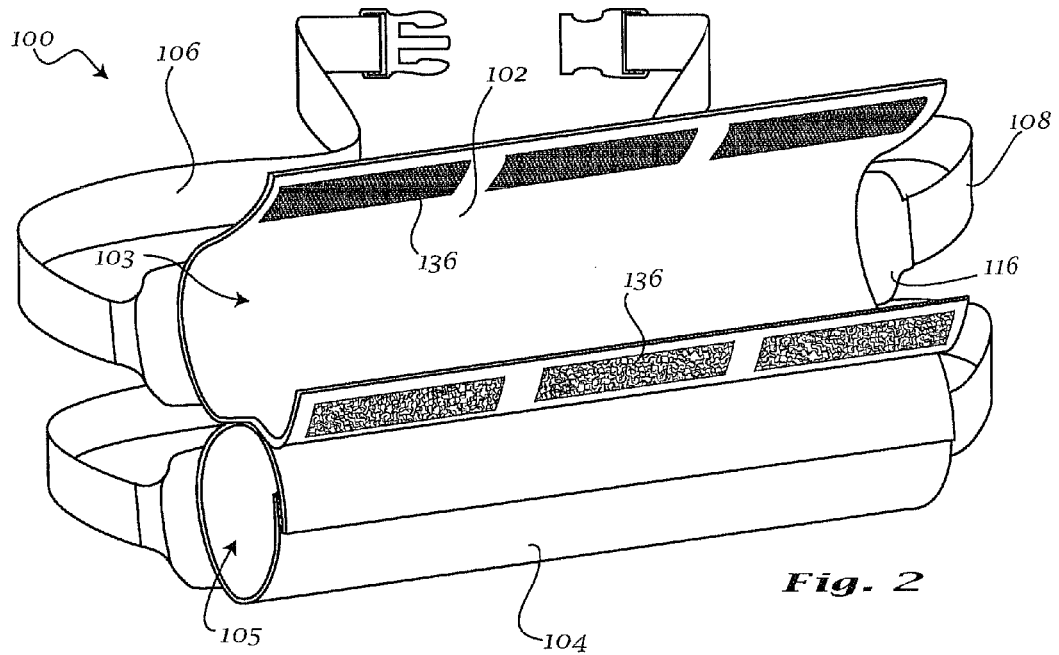
FIG. 2 is a front view of an exemplary embodiment of an arm sling in a partially opened configuration.
Figure 3:
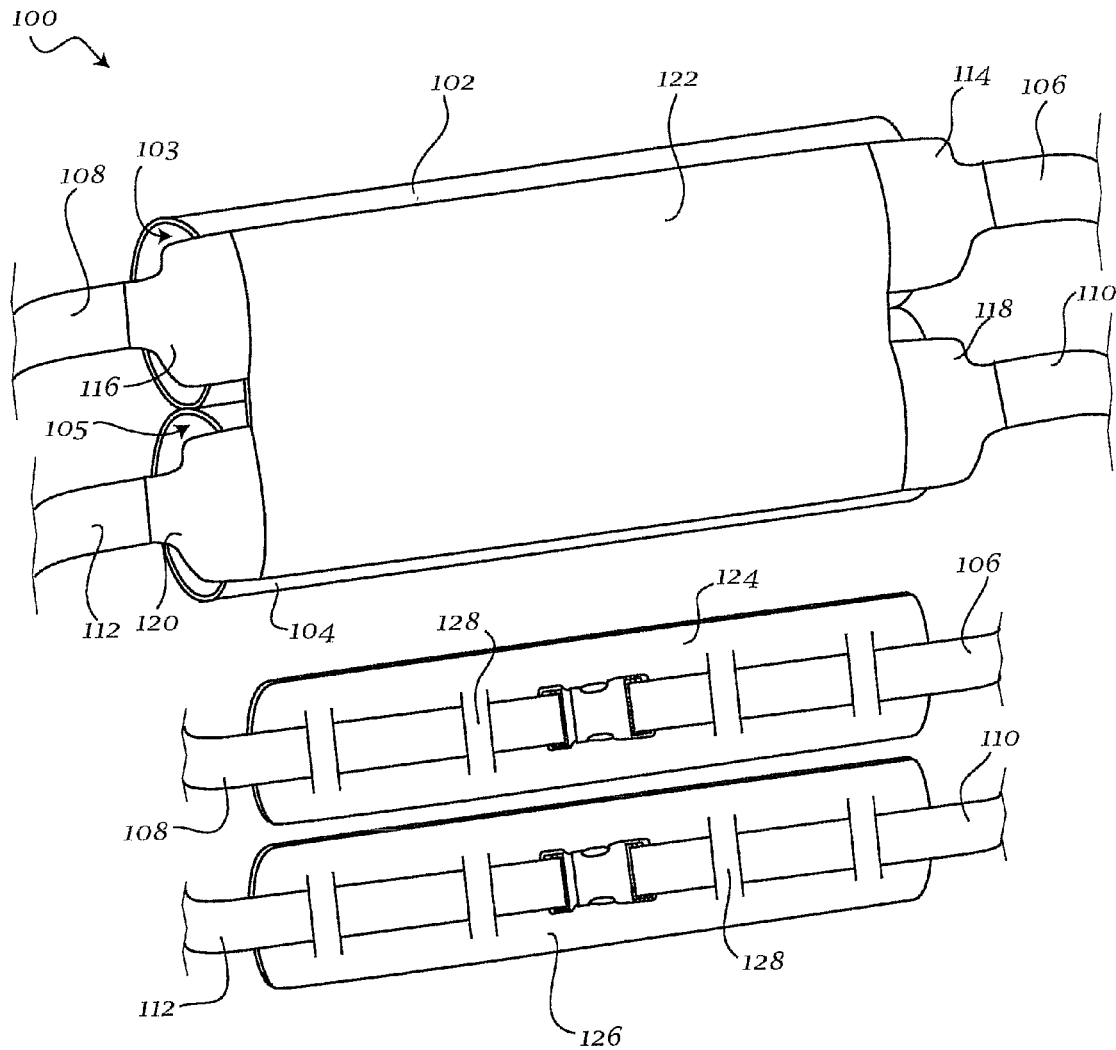
FIG. 3 is a rear view of an exemplary embodiment of an arm sling including a pair of back pads.

Turning to FIGS. 1-3, an exemplary double arm sling 100 is shown. Arm sling 100 may include an upper arm pouch 102, a lower arm pouch 104, two upper half-straps 106, 108 and two lower half-straps 110, 112. Arm pouches 102, 104 may each be formed from a single sheet of material that is rolled into a cylinder or tube-like shape, thereby defining upper cavity 103 within upper arm pouch 102 and lower cavity 105 within lower arm pouch 104. The single sheet of material may be rolled into a cylinder shape such that the edges of the sheet meet and overlap substantially near the front of arm sling 100. The arms of the patient may be received within cavities 103, 105. Arm pouches 102, 104 may be constructed of a synthetic or natural fabric, woven material, polymer based material, or any other material that enables arm sling 100 to function as described herein. Arm pouches 102, 104 may further include padding or any other resilient material known in the art. Half-straps 106, 108, 110, 112 may be constructed of an elastic material, a fabric material, a woven material, or any similar strap material known in the art. Half-straps 106, 108, 110, 112 may further be adjustable, such that half-straps 106, 108, 110, 112 may be lengthened or shortened as desired to facilitate snugly and comfortably fitting arm sling 100 around the torso of a patient.

Left upper half-strap 106 may be coupled to left upper tongue 114, and left upper tongue 114 may in turn be coupled to upper arm pouch 102. Right upper half-strap 108 may be coupled to right upper tongue 116, and left upper tongue 116 may in turn be coupled to upper arm pouch 102. Left lower half-strap 110 may be coupled to left lower tongue 118, and left lower tongue 118 may in turn be coupled to lower arm pouch 104. Right lower half-strap 112 may be coupled to left lower tongue 120, and left lower tongue 120 may in turn be coupled to lower arm pouch 104. Coupling between the straps, tongues and pouches of arm sling 100 may be facilitated by stitching, adhesives, or any other coupling techniques known in the art. The tongues 114, 116, 118, 120 may be constructed of the same or similar material as arm pouches 102, 104. In one embodiment, tongues 114, 116, 118, 120 may have a reduced thickness compared to the thickness of arm pouches 102, 104, in order to facilitate the flexing of tongues 114, 116, 118, 120 without imparting flex to arm pouches 102, 104. The straps can thus be tightly fastened around the torso of the patient without distorting the cylindrical shape of arm pouches 102, 104.

In one exemplary embodiment, double arm sling 100 may also include a backing portion 122. Upper arm pouch 102 and lower arm pouch 104 may both be coupled to backing portion 122. Upper arm pouch 102 and lower arm pouch 104 can thus be maintained in the same position relative to each other when double arm sling 100 is worn by a patient. Backing portion 122 may be constructed of a synthetic or natural fabric, woven material, polymer based material, or any other material that enables arm sling 100 to function as described herein. Backing portion 122 may further include padding or any other resilient material known in the art in order to facilitate providing comfort for the patient wearing arm sling 100. Each of left upper tongue 114, right upper tongue 116, left lower tongue 118 and right lower tongue 120 may be coupled to backing portion 120. Coupling between the backing portion 122, as well as the tongues and pouches of arm sling 100 may be facilitated by stitching, adhesives, or any other coupling techniques known in the art. In another exemplary embodiment, backing portion 120 may have a shape having tongue portions 114, 116, 118, 120 defined in the perimeter thereof, thereby reducing the number of components needed to manufacture arm sling 100.

Left upper half-strap 106 and right upper half-strap 108 may be fastened to each other via any method of fastening known in the art, such as, for example, a snap buckle having a male portion 130 and a female portion 132. Left lower half-strap 110 and right lower half-strap 112 may be fastened to each other in a similar manner. In one exemplary embodiment, arm sling 100 may further include an upper back pad 124 and a lower back pad 126. Back pads 124, 126 may include belt loops 128 through which half-straps 106, 108, 110, 112 may be threaded prior to fastening. Back pads 124, 126 may be constructed of a synthetic or natural fabric, woven material, polymer based material, or any other material that enables arm sling 100 to function as described herein. Back pads 124, 126 may further include padding or any other resilient material known in the art in order to facilitate providing comfort for the patient wearing arm sling 100.

Upper arm pouch 102 and lower arm pouch 104 may further include a plurality of fasteners 136 disposed thereon. Fasteners 136 may be any fasteners known in the art, such as, for example, Velcro-style hook-and-loop fasteners, buttons, snaps, magnets, zippers, and so forth. Fasteners 136 may be disposed substantially near the edges of the sheet of material from which upper arm pouch 102 or lower arm pouch 104 is formed.

In an exemplary method of using an arm sling 100, the arm sling 100 may be placed on a patient by a caretaker. The caretaker may place arm sling 100 substantially near the abdominal region of the patient, such that arm pouches 102, 104 are facing forward. The caretaker may then wrap half-straps 106, 108, 110, 112 around the patient's torso and fasten together left upper half-strap 114 and right upper half-strap 116, as well as left lower half-strap 118 and right lower half-strap 120. In one exemplary embodiment, the caretaker may also thread upper half-straps 106, 108 through upper back pad 124 and lower half-straps 110, 112 through lower back pad 126, thereby facilitating the distribution of weight through a larger area and reducing the pressure on the patient's back. The caretaker may then adjust the lengths of half-straps 106, 108, 110, 112 such that arm sling 100 is snugly fastened around the patient's torso.

Once arm sling 100 is secured around the patient's torso, the caretaker may disconnect fasteners 136 of upper arm pouch 102, thereby opening upper arm pouch 102. One of the patient's arms may then be placed into cavity 103, subsequent to which the caretaker may close upper arm pouch 102 and connect fasteners 136, thereby securing the patient's arm within upper arm pouch 102. The caretaker may then disconnect fasteners 136 of lower arm pouch 104, thereby opening lower arm pouch 104. The other of the patient's arms may then be placed into cavity 105, subsequent to which the caretaker may close lower arm pouch 104 and connect fasteners 136, thereby securing the patient's arm within lower arm pouch 104. Consequently, both arms of the patient are secured within arm pouches 102, 104 of arm sling 100. The weight of the patient's arms is distributed through half-straps 106, 108, 110, 112 and back pads 124, 126, thereby minimizing the strain to the patient's shoulder and neck area. It should be appreciated that the separate arm pouches allow the caretaker to individually tend to each of the patient's arms and secure each arm in its respective pouch. Consequently, in contrast to a single-pouch sling, the separate pouches reduce the likelihood of a patient's arm being displaced from the pouch while the other arm is being tended to or placed into the pouch. Therefore, the use of a double arm sling may minimize further discomfort and embarrassment to the patient, as well as reduce extra effort to the caretaker.

Figure 4:
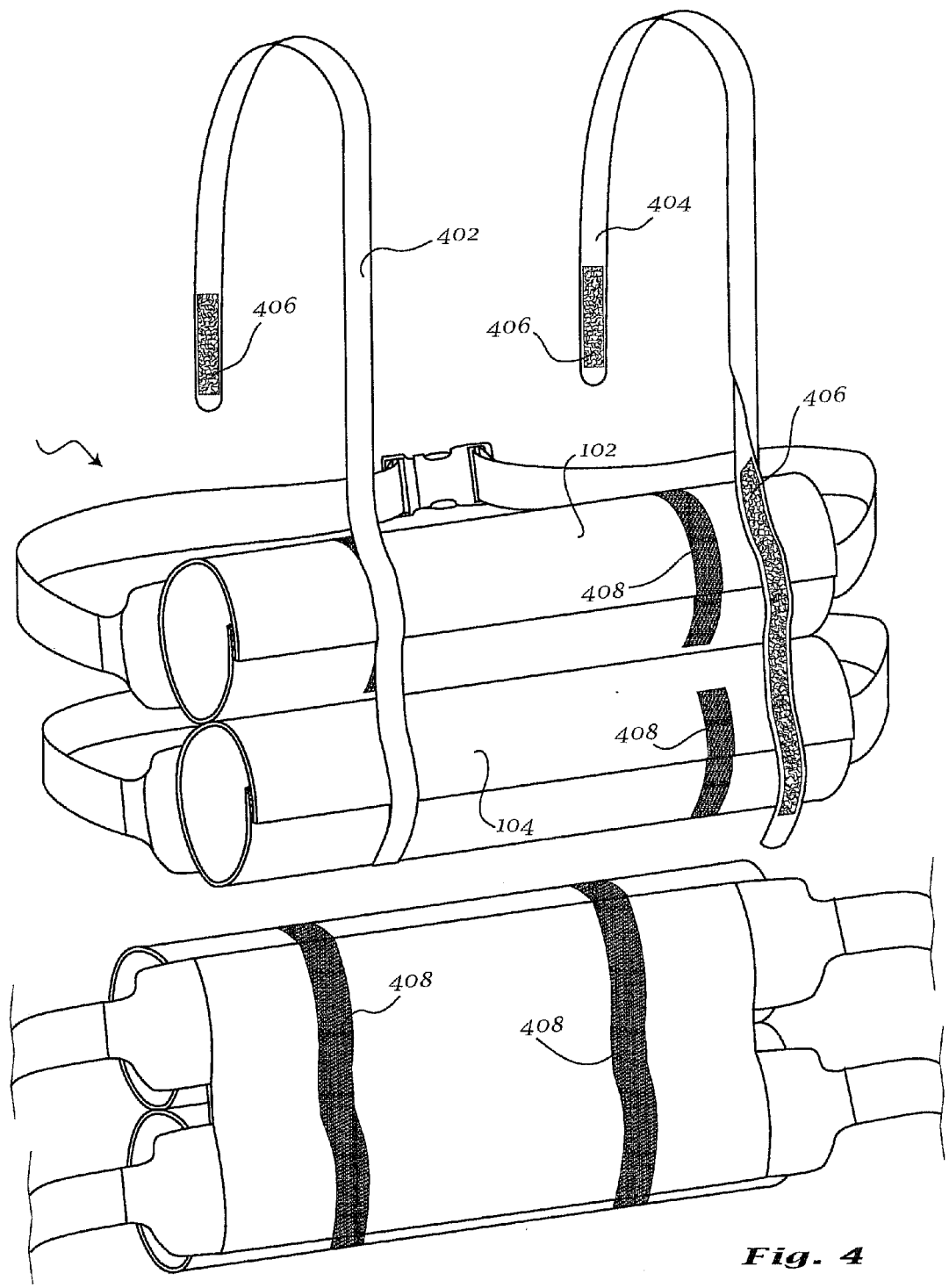
FIG. 4 is a front and rear view of another exemplary embodiment of an arm sling.

Turning to FIG. 4, another exemplary embodiment of double arm sling 100 is shown. In the exemplary embodiment, double arm sling 100 may further include two shoulder straps 402, 404. Patients who are not suffering from subluxation of the shoulder joints or weakness of the neck may desire additional support provided by shoulder straps 402, 404. Shoulder straps 402, 404 may be constructed of an elastic material, a fabric material, a woven material, or any similar strap material known in the art. Shoulder straps 402, 404 may further be adjustable, such that shoulder straps 402, 404 may be lengthened or shortened as desired to facilitate snugly and comfortably fitting arm sling 100 around the torso of a patient.

Shoulder straps 402, 404 may include a plurality of fasteners 406 disposed thereon. Arm sling 100 may likewise have a plurality of fasteners 408 disposed thereon. Fasteners 406, 408 may be any fasteners known in the art, such as, for example, Velcro-style hook-and-loop fasteners, buttons, snaps, magnets, zippers, and so forth. Fasteners 408 may be disposed on arm sling 100 such that they correspond to fasteners 406 disposed on shoulder straps 402, 404. For example, fasteners 406 disposed on the front portions of straps 402, 404 may couple to fasteners 408 on the front-facing portion of arm sling 100. Similarly, fasteners 406 disposed on the rear portions of straps 402, 404 may couple to fasteners 408 disposed on back pads 124, 128. In one embodiment, fasteners 408 may likewise be disposed on the patient-facing portion of arm sling 100 to further facilitate securing arm sling 100 to a garment worn by the patient.

Figure 5:
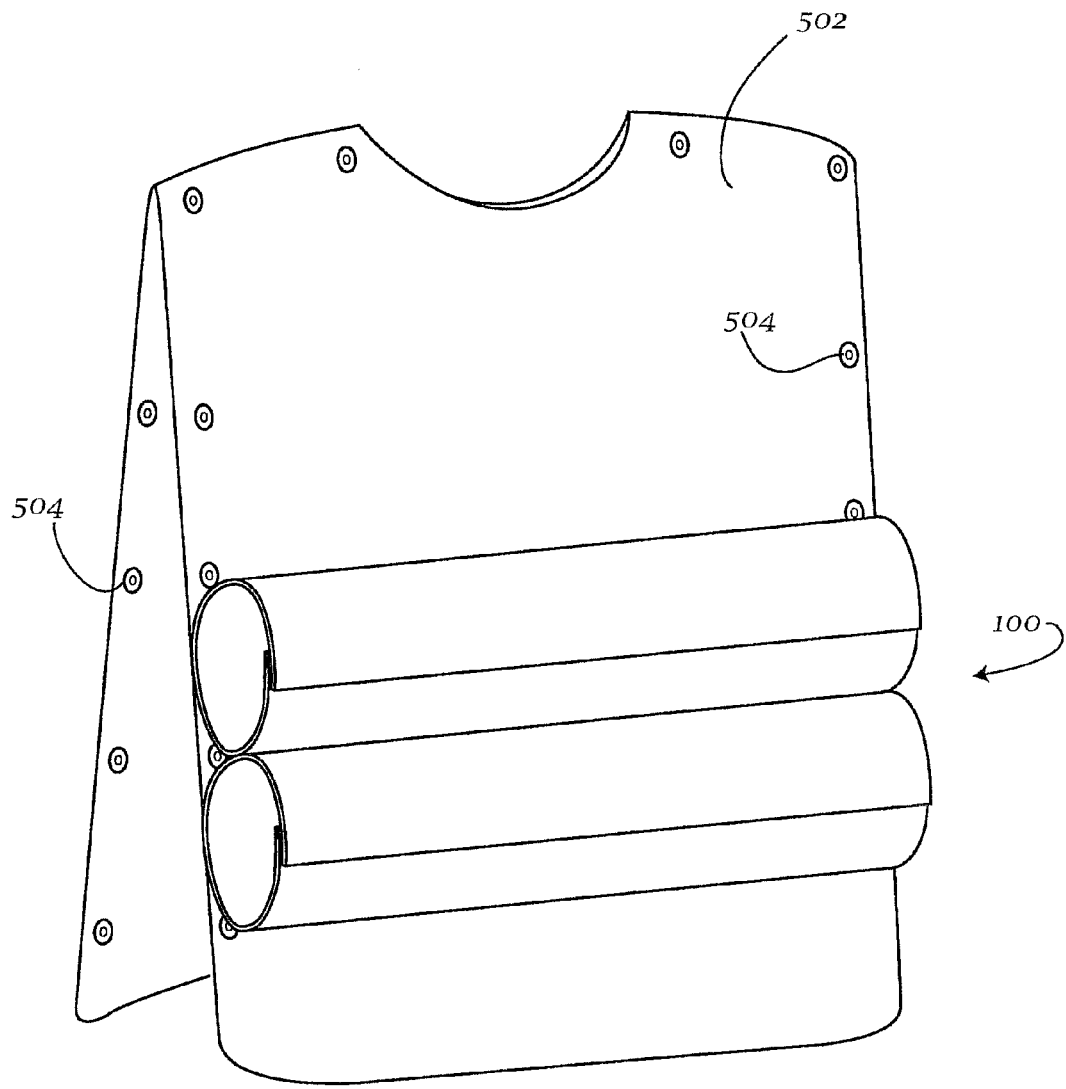
FIG. 5 is a front view of another exemplary embodiment of an arm sling.

Turning to FIG. 5, another exemplary embodiment of double arm sling 100 is shown. In the exemplary embodiment, double arm sling 100 may further include a garment 502. Garment 502 may be a vest, shirt, T-shirt, or any other garment known in the art that enables arm sling 102 to function as described herein. Garment 502 may further include a plurality of fasteners 504 disposed thereon. Fasteners 504 may be any fasteners known in the art, such as, for example, Velcro-style hook-and-loop fasteners, buttons, snaps, magnets, zippers, and so forth. Fasteners 504 may be used to couple the front and back portions of garment 502. Similarly, fasteners 504 may be disposed on the patient-facing portion of arm sling 100 may be used to couple arm sling 100 to garment 502.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A double arm sling, comprising:
   two pouches, each of the two pouches configured for individually receiving one of a patient's arms;
   at least one pair of half-straps, the at least one pair of half-straps configured to fasten the double arm sling around the torso of the patient,
   at least one pair of tongues coupled to the two pouches and coupled to the at least one pair of half-straps;
   a backing portion coupled to the two pouches; and
   at least one back pad configured to receive the at least one pair of half straps.

2. The arm sling of claim 1, wherein each of the two pouches is selectively sealable.

3. The arm sling of claim 2, further comprising a plurality of fasteners disposed on each of the two pouches for selectively sealing each of the two pouches.

4. The arm sling of claim 3, wherein the fasteners are Velcro.

5. The arm sling of claim 3, wherein the fasteners are snaps.

6. The arm sling of claim 1, wherein each of the two pouches is formed from a single sheet of material.

7. The arm sling of claim 6, further comprising a plurality of fasteners disposed substantially near the edge of the single sheet of material.

8. The arm sling of claim 1, further comprising a pair of shoulder straps selectively coupleable to the two pouches and to the at least one back pad.

* * * * *